(12) United States Patent
Tsuboi et al.

(10) Patent No.: US 10,018,548 B2
(45) Date of Patent: Jul. 10, 2018

(54) MEASUREMENT DEVICE, MEASUREMENT SYSTEM, AND MEASUREMENT METHOD FOR MEASURING PARTICLE AND GAS

(71) Applicant: FUJITSU LIMITED, Kawasaki-shi, Kanagawa (JP)

(72) Inventors: Osamu Tsuboi, Kawasaki (JP); Michio Ushigome, Atsugi (JP); Satoru Momose, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/398,887

(22) Filed: Jan. 5, 2017

(65) Prior Publication Data

US 2017/0115196 A1    Apr. 27, 2017

Related U.S. Application Data

(63) Continuation of application No. PCT/JP2014/069702, filed on Jul. 25, 2014.

(51) Int. Cl.
*G01N 15/02* (2006.01)
*G01N 25/18* (2006.01)
*G01N 27/16* (2006.01)
*G01N 15/14* (2006.01)

(52) U.S. Cl.
CPC ..... *G01N 15/0205* (2013.01); *G01N 15/1404* (2013.01); *G01N 25/18* (2013.01); *G01N 27/16* (2013.01)

(58) Field of Classification Search
CPC ................................................ G01N 15/0205
USPC ........................................................ 356/338
See application file for complete search history.

(56) References Cited

U.S. PATENT DOCUMENTS

| | | | | |
|---|---|---|---|---|
| 6,422,060 | B1 * | 7/2002 | Patashnick | G01N 15/02 73/28.01 |
| 2005/0264810 | A1 * | 12/2005 | Saito | G01N 15/0211 356/338 |
| 2008/0170226 | A1 * | 7/2008 | Moriya | C23C 16/4412 356/338 |
| 2012/0315567 | A1 * | 12/2012 | Ueda | H01M 8/1004 429/481 |

FOREIGN PATENT DOCUMENTS

JP    H05-027654    4/1993
JP    2001-296264 A    10/2001
(Continued)

OTHER PUBLICATIONS

Office Action of JP Patent Application No. 2016-535611 dated Sep. 5, 2017 (3 Sheets, 4 Sheets translation, 7 Sheets total).
(Continued)

*Primary Examiner* — Tarifur Chowdhury
*Assistant Examiner* — Omar Nixon
(74) *Attorney, Agent, or Firm* — Kratz, Quintos & Hanson, LLP

(57) ABSTRACT

A measurement device includes a first flow passage, a heating unit provided on one end side of the first flow passage, a gas detection unit provided on one end side of the first flow passage and capable of detecting a gas through heat applied from the heating unit, and a particle measurement unit which optically measures, at an upper side than the heating unit of the first flow passage, particles passing through the first flow passage.

10 Claims, 12 Drawing Sheets

(56) References Cited

FOREIGN PATENT DOCUMENTS

| JP | 2002-501187 A1 | 1/2002 |
| JP | 2006-003090 A1 | 1/2006 |
| JP | 2007-017208 A | 1/2007 |
| JP | 2007-101459 A | 4/2007 |
| JP | 2007-147437 A1 | 6/2007 |
| JP | 2010-256052 A1 | 11/2010 |
| JP | H07-311171 A | 9/2017 |

OTHER PUBLICATIONS

International Search Report for International Application No. PCT/JP2014/069702 dated Oct. 28, 2014.
Written Opinion of the International Searching Authority for International Application No. PCT/JP2014/069702 dated Oct. 28, 2014 (4 Sheets, 2 Sheets translation; 6 Sheets total).

* cited by examiner

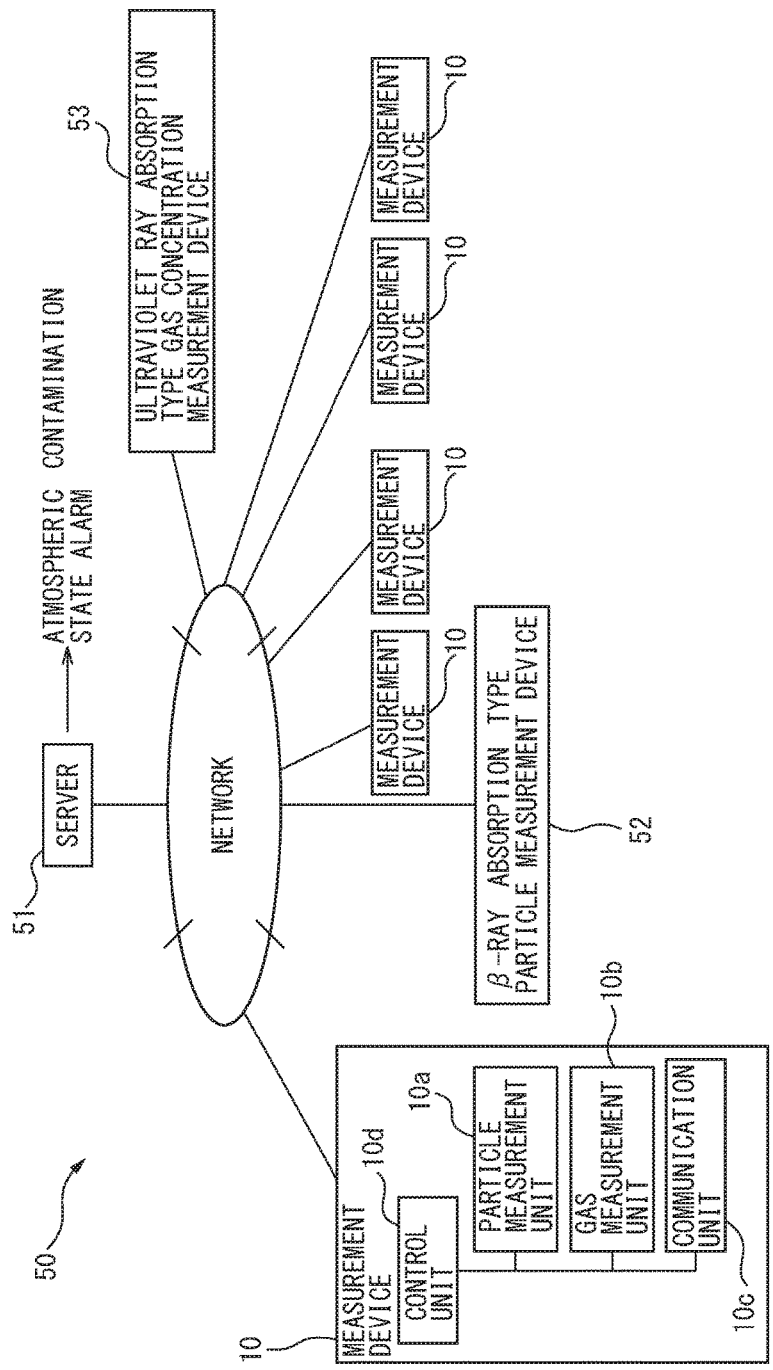

MEASUREMENT DEVICE, MEASUREMENT SYSTEM, AND MEASUREMENT METHOD FOR MEASURING PARTICLE AND GAS

This application is based upon and claims the benefit of priority of the International Application PCT/JP2014/069702, filed on Jul. 25, 2014 and designated the U.S. the entire contents of which are incorporated herein by reference.

FIELD

The present invention relates to a measurement device, measurement system, and measurement method for measuring particle and gas.

BACKGROUND

In recent years, in conjunction with development of industries and multipoint progress of manufacturing industries, air pollution on a global scale has been feared. For example, respiratory diseases due to particulate matter in suspension (Suspended Particulate Matter: SPM or particulate matter: PM 2.5) or ground level ozone can be mentioned. According to an environmental outlook to 2050 published in 2012 by the Organization for Economic Co-operation and Development (OECD) which is an international organization, with regard to children early deaths, aspiratory diseases due to such atmospheric contaminants will increase over the next few decades. In other words, as causes of global health problems, air pollution is a matter of concern. Such air pollution is expected to be higher in China or developing countries in South Asia, etc.

Also in our country, with respect to suspended particulate matter and photochemical oxidants (as principal substances, ozone and the like are included), locations showing an excess over environmental standards have been appearing.

Measuring atmospheric contaminants, such as suspended particulate matter and photochemical oxidants, and taking countermeasures based on measurement results is necessary.

For example, in our country, environmental monitoring stations at which each municipality measures atmospheric contaminants are set up throughout the country and a system connecting each of the environmental monitoring stations is used to monitor air pollution. Specifications of a measurement device for measuring atmospheric contaminants are determined under official regulations, and accuracy of the measurement results is secured.

For example, to measure suspended particulate matter, such as SPM or PM 2.5, the measurement device which is of a β-ray absorption type is used.

Patent literature 1: Japanese Unexamined Patent Publication (Kokai) No. 2002-501187
Patent literature 2: Japanese Unexamined Patent Publication (Kokai) No. 2007-147437
Patent literature 3: Japanese Unexamined Patent Publication (Kokai) No. 2006-3090

SUMMARY

However, although the β-ray absorption type measurement device in accordance with the official method has high measurement accuracy, the device is large and consumes a large amount of electric power. Consequently, a measurement device which is small and consumes a small amount of electric power has been sought.

As a particle measurement device which is small and consumes a small amount of electric power, using a particle measurement device which is of an optical type has been proposed. The optical type particle measurement device includes, for example, a flow passage through which particles are carried by an air stream to pass, a light-emitting element which irradiates the flow passage with light, and a light-receiving element which receives scattering light as scattered by particles. The optical type particle measurement device measures scattering light due to particles or the like, thereby able to measure a particle concentration and a particle size distribution.

As a method of generating an air stream in the flow passage, a pump or a heater to generate an air stream is employed.

When the pump is used to generate an air stream, for example, it is necessary to provide a filter or a particle sizer which removes particles having a particle size larger than 10 μm.

On the other hand, when the heater is used, an ascending air stream is made to occur toward a direction opposite to gravitation, which makes it difficult to generate such a stream speed that is capable of carrying particles having a large particle size, and therefore providing a filter or a particle sizer is not necessary. However, to drive the heater, a large amount of electric power is necessary. For example, from electric power of 900 mW which is consumed by the measurement device, 600 mW is used as electric power for the heater.

Further, as the measurement device which measures atmospheric contaminants, measuring particles while measuring a gas, such as ozone, at the same time are required. As gaseous atmospheric contaminants, for example, general ozone, an oxide gas of sulfur or nitrogen, hydrogen sulfide in a hot spring or a sewer pipe, and a volatile organic compound (VOC), such as formaldehyde, in a room can be cited.

As a device having high gas measurement accuracy, for example, there is an ultraviolet ray absorption type gas concentration measurement device, but such device is large and consumes a large amount of electric power.

As a gas measurement device which is small and consumes small electric power, a gas measurement device including a gas detection unit formed with a semiconductor in which a gas is adsorbed, whereby an electric resistance changes has been proposed.

In such gas measurement device, a surface of the gas detection unit is disposed in such a manner as to be exposed to a flow passage through which a gas flows. Further, using a pump or a heater, to the surface of the gas detection unit, the external air is supplied. When the pump is used, electric power for driving the heater is further necessary.

The flow passage used in gas measurement through which a gas flows and the flow passage through which, in particle measurement, particles are carried by an air stream to pass are to be separately provided such that each air stream does not interfere, which means that the size of the measurement devices which measure particles and gas is large.

In the present description, an object is to propose a measurement device for measuring particles and a gas which is capable of solving the problem as described above.

Moreover, in the present description, an object is to propose a measurement system for measuring particles and a gas which is capable of solving the problem as described above.

Further, in the present description, an object is to propose a measurement method for measuring particles and a gas which is capable of solving the problem as described above.

According to an aspect of the measurement device for measuring particles and a gas as disclosed in the present description, a measurement device includes: a first flow passage; a heating unit provided on one end side of the first flow passage; a gas detection unit provided on the one end side of the first flow passage and capable of detecting a gas through heat applied from the heating unit; and a particle measurement unit which optically measures, at an upper side than the heating unit of the first flow passage, particles passing through the first flow passage.

According to an aspect of the measurement system for measuring particles and a gas as disclosed in the present description, a measurement system includes: a plurality of measurement devices, the measurement devices including: a first flow passage; a heating unit provided on one end side of the first flow passage; a gas detection unit provided on the one end side of the first flow passage and capable of detecting a gas through heat applied from the heating unit; and a particle measurement unit which optically measures, at an upper side than the heating unit of the first flow passage, particles passing through the first flow passage; and a server communicably connected to each measurement device.

According to an aspect of the measurement method for measuring particles and a gas as disclosed in the present description, a measurement method of a measurement device, in which the measurement device includes: a first flow passage; a heating unit provided on one end side of the first flow passage; a gas detection unit provided on the one end side of the first flow passage and capable of detecting a gas through heat applied from the heating unit; and a particle measurement unit which optically measures, at an upper side than the heating unit of the first flow passage, particles passing through the first flow passage, controls the heating unit such that a temperature of the gas detection unit differs depending on when particles are measured and when a gas is measured.

The object and advantages of the present invention will be realized and attained by means of the elements and combinations particularly pointed out in the claims.

It is to be understood that both the foregoing general illustration and the following detailed illustration are exemplary and illustrative and are not restrictive of the present invention as recited in the claims.

BRIEF DESCRIPTION OF DRAWINGS

FIG. 11 is a diagram of an embodiment of a measurement system disclosed in the present description.

DESCRIPTION OF EMBODIMENTS

Hereinafter, a preferable first embodiment of a measurement device disclosed in the present description will be illustrated with reference to the drawings. Note that the technical scope of the present invention is not limited to the embodiments herein but extends to the inventions as recited in the claims as well as equivalents thereof.

Figure 1:
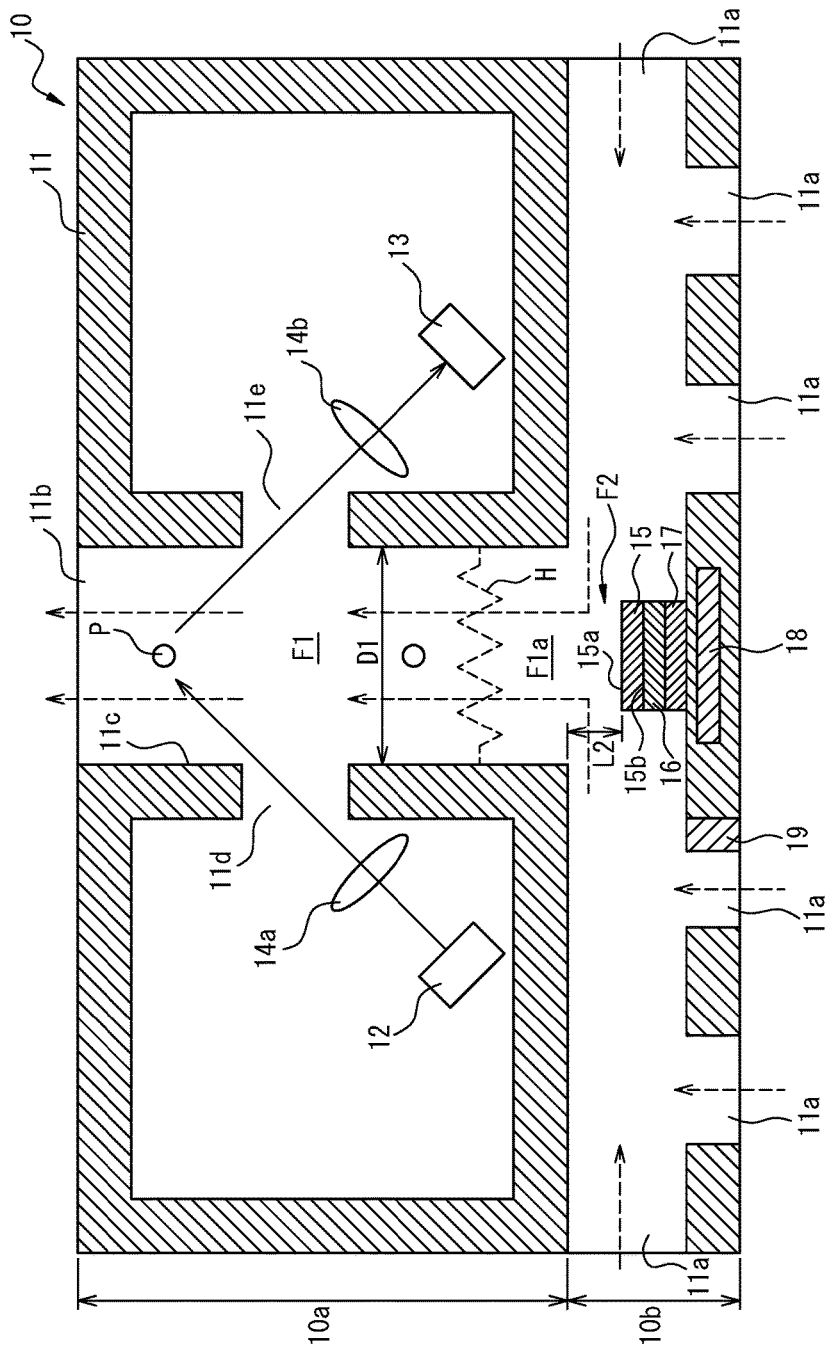
FIG. 1 is a cross-sectional view of a first embodiment of a measurement device disclosed in the present description.
Figure 2:
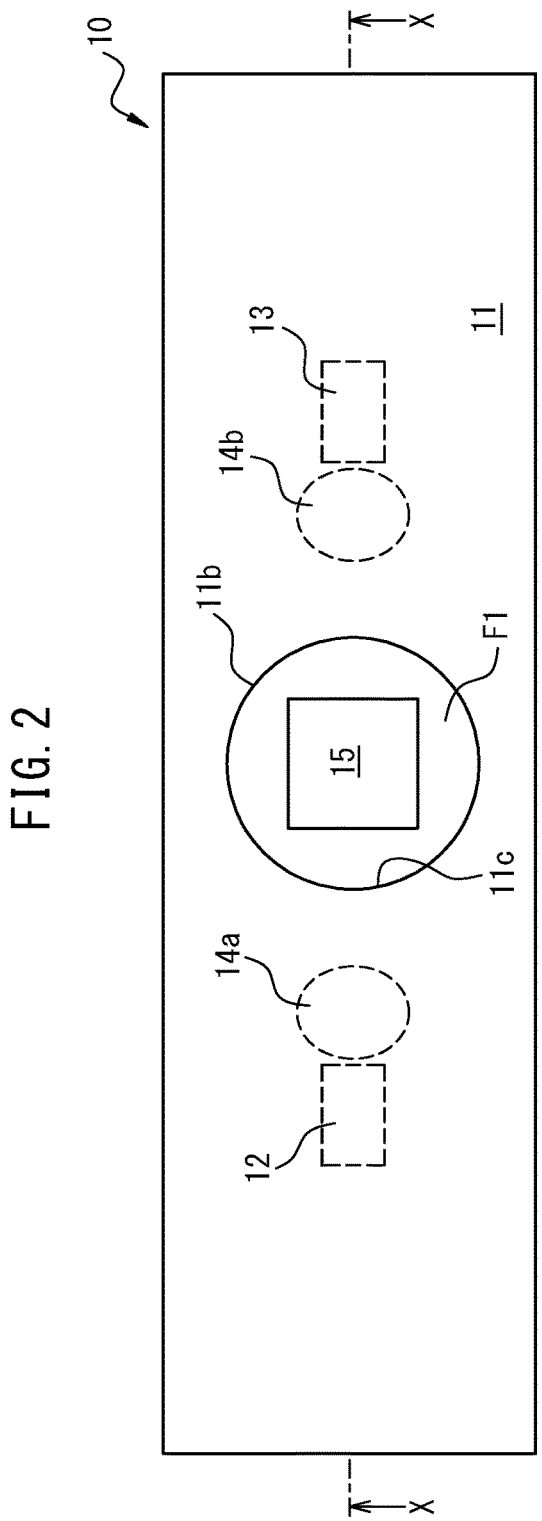
FIG. 2 is a plan view of the first embodiment of the measurement device disclosed in the present description.

FIG. 1 is a cross-sectional view of the first embodiment of the measurement device disclosed in the present description. FIG. 2 is a plan view of the first embodiment of the measurement device disclosed in the present description. FIG. 1 is the cross-sectional view taken along a line X-X of FIG. 2.

A measurement device 10 according to the present embodiment measures particles and a gas in the air.

The measurement device 10 includes a particle measurement unit 10a which measures a particle concentration and a particle size distribution in the air and a gas measurement unit 10b which measures a concentration of a predetermined gas in the air.

The particle measurement unit 10a optically measures particles passing through a first flow passage F1. Specifically, the particle measurement unit 10a includes a light-emitting element 12 which irradiates the first flow passage F1 through which a particle P is carried by an air stream to pass with light and a light-receiving element 13 which receives scattering light as scattered by the particle P passing through the first flow passage F1. The first flow passage F1, the light-emitting element 12, and the light-receiving element 13 are disposed in the interior of a housing 11.

The first flow passage F1 is a column-shaped space enclosed by a cylindrically-shaped inner wall 11c disposed in the interior of the housing 11. In the measurement device 10, the first flow passage F1 is preferably disposed in such a manner as to correspond to a perpendicular direction.

Light irradiated by the light-emitting element 12 is refracted through a lens 14a, passes through an opening 11d, and converges upon a predetermined area in the first flow passage F1. When the particle P passes through the predetermined area in the first flow passage F1, the particle P scatters light irradiated from the light-emitting element 12. From light scattered by the particle P, light which has passed an opening 11e is refracted through a lens 14b and received by the light-receiving element 13.

Each element is disposed such that an optical axis of light which is irradiated from the light-emitting element 12 and passes through the lens 14a and an optical axis of light which passes through the lens 14b and comes into the light-receiving element 13 intersect at right angles. Note that to receive light backscattered by the particle P as in the present embodiment, backscattered light may be reflected using a mirror and received by the light-receiving element.

The light-emitting element 12 and the lens 14a are disposed in a space enclosed by the housing 11, the inner wall 11c, and the like and prevented from being effected by light from the exterior. Similarly, the light-receiving element 13 and the lens 14b are disposed in a space enclosed by the housing 11, the inner wall 11c, and the like and prevented from being effected by light from the exterior.

The light-emitting element 12 and the light-receiving element 13 are controlled by an unillustrated control unit, an output signal of the light-receiving element 13 is analyzed by the control unit, and the particle concentration and the particle size distribution are determined.

The particle measurement unit 10a according to the present embodiment determines a particle size using the Mie scattering theory. The Mie scattering theory is preferably used when the particle size is equal to or slightly larger than a wavelength of light. When the particle size is sufficiently larger than the wavelength of light, the particle size is preferably measured using the laser diffraction method. In the present description, receiving scattering light as scattered by the particle P passing through the first flow passage F1 by the light-receiving element 13 includes receiving light diffracted or light reflected by the particle P.

In such an embodiment, it is known that a peak intensity of light diffracted or light reflected by the particle P increases in proportion to the square of the particle size. Further, since a speed at which the particle P passes through the first flow passage F1 is constant in accordance with a stream speed of an air stream, a time in which an electric signal from the light-receiving element 13 exceeds a threshold value based on which scattering light is determined to be present depends on the peak intensity. Thus, from a pulse width of the electric signal from the light-receiving element 13, the particle size can be estimated.

The gas measurement unit 10b includes a plurality of air inlet ports 11a for taking in the external air to a second flow passage F2.

Further, the gas measurement unit 10b includes a gas detection unit 15 which has a first surface 15a and a second surface 15b. The first surface 15a is exposed to the second flow passage F2 and a gas is adsorbed to the first surface 15a, whereby an electric resistance changes. The gas detection unit 15 has a layered shape, and the first surface 15a of the gas detection unit 15 is disposed in such a manner as to face an inlet F1a of the first flow passage F1.

The inlet F1a of the first flow passage F1 is connected to the second flow passage F2 of the gas measurement unit 10b. The second flow passage F2 supplies the external air to the inlet F1a on one end side of the first flow passage F1.

The gas measurement unit 10b includes a heating unit 17 which heats the second surface 15b of the gas detection unit 15. The heating unit 17 is formed, for example, using a resistor to which electric power is supplied to generate Joule heat. The heating unit 17 is provided at the inlet F1a on one end side of the first flow passage F1.

Between the gas detection unit 15 and the heating unit 17, an electrical insulation part 16 which electrically insulates both is disposed. The electrical insulation part 16 and the heating unit 17 also have a layered shape, and on an interior surface of the housing 11, the heating unit 17, the electrical insulation part 16, and the gas detection unit 15 are stacked in this order.

In the housing 11 on a side, with respect to the heating unit 17, opposite to the gas detection unit 15, a thermal insulation part 18 is disposed. The thermal insulation part 18 prevents heat generated by the heating unit 17 from conducting to the exterior and decreases electric power consumed by the heating unit 17. As the thermal insulation part 18, for example, an air layer or a porous body can be used.

The gas detection unit 15 can detect a gas through heat applied from the heating unit 17. In the gas detection unit 15, the second surface 15b is heated by the heating unit 17 and the first surface 15a is maintained to have a predetermined temperature (for example, 400° C.). On the first surface 15a, oxygen molecules as heated are activated to generate oxygen ions, and on the first surface 15a, an adsorption equilibrium state of the oxygen ions is formed. When the gas detection unit 15 is formed with a semiconductor having an n-type polarity, a depletion layer is formed in the vicinity of the surface of the semiconductor to which the oxygen ions are adsorbed and a concentration of electrons which are carriers decreases so that the electric resistance increases. On the other hand, when the gas detection unit 15 is formed with a semiconductor having a p-type polarity, holes which are carries are accumulated in the vicinity of the surface of the semiconductor to which the oxygen ions are adsorbed so that a hole concentration increases and accordingly the electric resistance decreases. Since the adsorption equilibrium state of the oxygen ions on the first surface 15a changes due to the presence of a gas, such as ozone, the electric resistance of the gas detection unit 15 changes in accordance with the gas concentration. Thus, by examining the electric resistance of the gas detection unit 15, the concentration of a gas present in the vicinity of the first surface 15a can be measured. An output signal of the gas detection unit 15 is analyzed by the unillustrated control unit, and the gas concentration is determined.

As a material which forms the gas detection unit 15, for example, a semiconductor formed of an oxide or a nitride of a metal, such as tin, zinc, or tungsten, or a semiconductor of carbon or the like can be used. To enhance gas selectivity of the gas detection unit 15, a noble metal, such as platinum, may be contained in a semiconductor.

In the present embodiment, the second flow passage F2 of the gas measurement unit 10b is formed by a space between the first surface 15a of the gas detection unit 15 and the inlet F1a of the first flow passage F1.

A gas in the second flow passage F2 is heated by the first surface 15a of the gas detection unit 15 heated by the heating unit 17 to form an ascending air stream which ascends in the first flow passage F1. Toward the second flow passage F2 which comes under a negative pressure due to the ascending air stream which ascends in the first flow passage F1, the external air passes through the air inlet ports 11a, as depicted by the arrows in FIG. 1, and flows. The external air taken in through the air inlet ports 11a passes through the second flow passage F2 to move to the first flow passage F1, and is then discharged through an air outlet port 11b to the exterior. At an upper side than the heating unit 17 of the first flow passage F1, the particle measurement unit 10a optically measures particles passing through the first flow passage F1.

Thus, in the measurement device 10 according to the present embodiment, an air stream which flows through the first flow passage F1 is formed based on heat generated by the heating unit 17 of the gas measurement unit 10b. Further, an air stream which flows over the first surface 15a of the gas detection unit 15 of the gas measurement unit 10b is also formed based on heat generated by the heating unit 17.

A gas, such as suspended particulate matter or ozone, contained in the external air is taken in together with the external air from the air inlet ports 11a into the housing 11.

A gas, such as ozone, is measured by the first surface 15a of the gas detection unit 15 which is exposed to the second flow passage F2. Further, suspended particulate matter is measured by the particle measurement unit 10a while being carried by the ascending air stream to pass through the first flow passage F1.

At an inner side of one of the air inlet ports 11a, a temperature and humidity measurement unit 19 which measures a temperature and a humidity of the external air is disposed. The unillustrated control unit controls the heating unit 17 based on the temperature and the humidity measured by the temperature and humidity measurement unit 19. When the temperature of the external air is high, the unillustrated control unit reduces a quantity of heat generated by the heating unit 17 and decreases consumed electric power of the heating unit 17. Further, when the humidity of the external air is high, particles containing moisture expand. The unillustrated control unit may adjust the quantity of generated heat of the heating unit 17 based on the humidity of the external air in such a manner that a humidity in the first flow passage F1 is constant so that an expansion state of particles is constant.

Note that in the present embodiment, the measurement device 10 includes the temperature and humidity measurement unit 19 in which a temperature measurement part and a humidity measurement part are unified, but the temperature measurement part and the humidity measurement part may be separate.

The ascending air stream formed in the first flow passage F1 is preferably formed in such a manner as to have a flow rate capable of carrying particles having a particle size in a measurement target. From such point of view, a distance L2 between the first surface 15a of the gas detection unit 15 which is exposed to the second flow passage F2 and a portion of the second flow passage F2 opposite to the first surface is preferably smaller than a first circle reduced diameter D1 when a cross-sectional shape of the first flow passage F1 is circular. Herein, a cross section of the first flow passage F1 signifies a surface orthogonal to a longitudinal direction of the first flow passage F1 (direction in which the gas flows). Further, the portion of the second flow passage F2 opposite to the first surface is, in the present embodiment, the inlet F1a of the first flow passage F1. The inlet F1a of the first flow passage F1 is a portion enclosed by an end edge of the inner wall 11c. Moreover, even when values of the distance L2 or the first circle reduced diameter D1 is not a constant, a relationship in which the distance L2 is smaller than the first circle reduced diameter D1 is preferably satisfied.

Hereinafter, the above relationship between the distance L2 and the first circle reduced diameter D1 will be illustrated with reference to the drawings.

Figure 3:
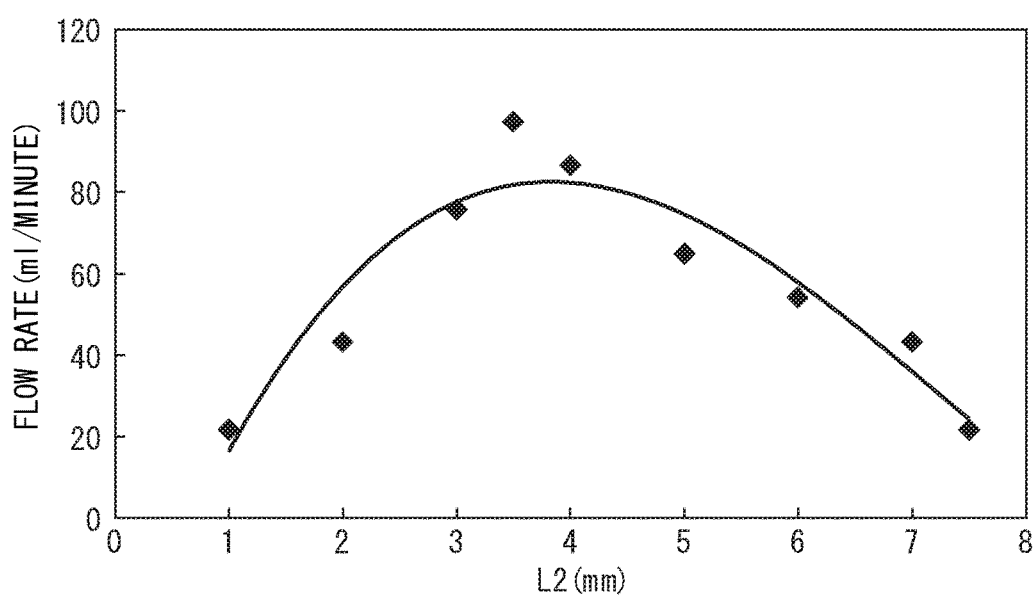
FIG. 3 is a diagram of a relationship between a distance L2 and a flow rate of a first flow passage.

FIG. 3 is a diagram of a relationship between the distance L2 and a flow rate of the first flow passage.

FIG. 3 illustrates results of measurement of a flow rate of a gas flowing through the first flow passage F1 when the distance L2 between the first surface 15a of the gas detection unit 15 and the inlet F1a of the first flow passage F1 is changed.

Since the first flow passage F1 had a column shape having a diameter of 9 mm, the first circle reduced diameter D1 was 9 mm. A length of the first flow passage F1 was 50 mm. To the resistor forming the heating unit 17, electric power of 400 mW was supplied, and the heating unit 17 was heated.

As depicted in FIG. 3, the distance L2 was changed within a range between 1 mm and 7.5 mm. Accordingly, the flow rate of a gas flowing through the first flow passage F1 indicated a peak in which the flow rate was approximately 100 ml/minute when the distance L2 ranges between 3 mm and 4 mm.

A reason why when the distance L2 becomes large, the flow rate decreases can be considered that since the distance L2 becomes greater than a thickness of a temperature boundary layer, heat of the first surface 15a of the gas detection unit 15 becomes difficult to be transferred to a gas in the second flow passage F2.

On the other hand, a reason why when the distance L2 becomes small, the flow rate decreases can be considered that since a volume of the second flow passage F2 decreases, in a flow passage through which flow is made from the air inlet ports 11a to the first flow passage F1, a pressure drop of the second flow passage F2 increases. Accordingly, it is considered that when the distance L2 is small, to a gas in the second flow passage F2, heat of the first surface 15a of the gas detection unit 15 is transferred, whereas the flow rate of the first flow passage F1 does not increase.

Thus, from the point of view of obtaining a large flow rate of the first flow passage F1, it is considered that the distance L2 is preferably configured to have approximately the thickness of the temperature boundary layer. Specifically, the distance L2 between the first surface 15a of the gas detection unit 15 which is exposed to the second flow passage F2 and the portion of the second flow passage F2 opposite to the first surface is preferably configured to fall within a range between 2/8 and 7/8 of the first circle reduced diameter D1 of the first flow passage F1. Particularly, the distance L2 is preferably configured to fall within a range between 3/8 and 5/8, further within a range between 3/8 and 4/8 of the first circle reduced diameter D1.

Figure 4A:
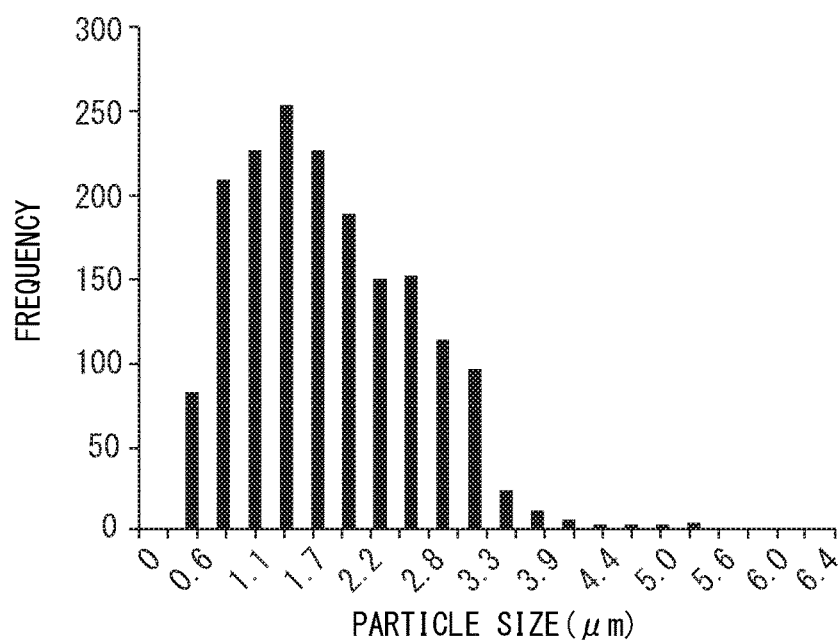
FIG. 4A is a diagram (No. 1) of measurement results of a particle size distribution.

Next, when the distance L2 is configured to be 3.5 mm, results of measurement of the particle size distribution are illustrated in FIG. 4A.

In the same conditions as in FIG. 3, the measurement device 10 was operated, the external air was introduced into the housing 11, and the particle size distribution was measured. FIG. 4A indicates a peak of distribution approximately when the particle size is 1 μm to 2 μm. Thus, it is understood that the measurement device 10 can perform measurement of particles of PM 2.5.

Figure 4B:
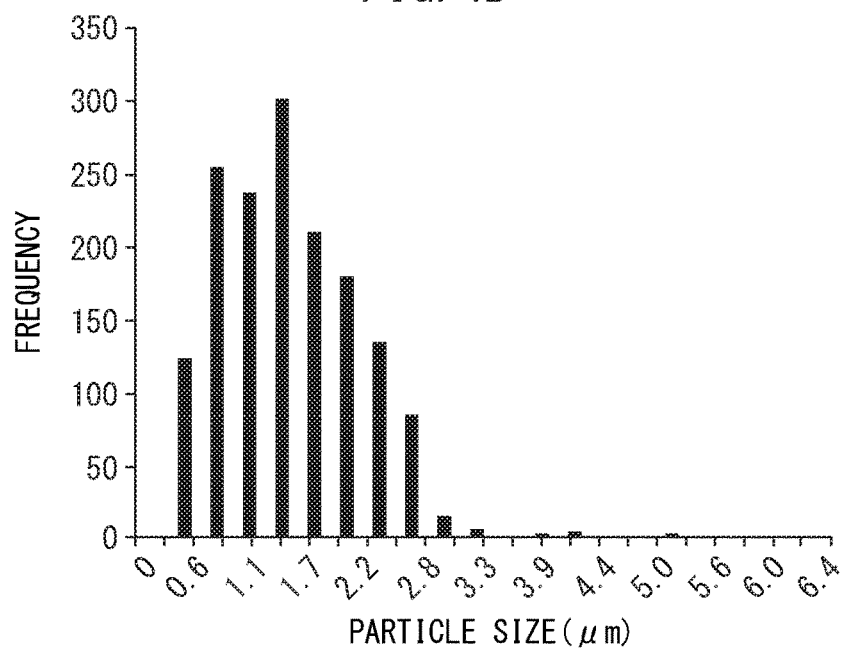
FIG. 4B is a diagram (No. 2) of measurement results of the particle size distribution.

Next, instead of generating an air stream in the first flow passage F1 using the heating unit 17, a heater H (see the chain line H in FIG. 1) was disposed in the vicinity of the inlet F1a of the first flow passage F1, the heater H was supplied with electric power of 400 mW to generate heat, and measurement of the particle size distribution was performed using the particle measurement unit 10a. FIG. 4B illustrates measurement results. Thus, disposing the heater in the first flow passage F1 to form an ascending air stream is a configuration used also in conventional particle measurement devices.

The measurement results in FIG. 4B indicate, similarly to the measurement results in FIG. 4A, a peak of distribution approximately when the particle size is 1 μm to 2 μm and illustrate the generally similar particle size distribution. Thus, it is understood that similarly to the heater H disposed in the vicinity of the inlet F1a of the first flow passage F1, the heating unit 17 can form an air stream for measuring particles in the first flow passage F1. Compared further in detail, the measurement results in FIG. 4A are different, in comparison with the measurement results in FIG. 4B, in that the distribution of particle size shifts in a direction to be larger by approximately 10%. Correcting such shift will be later described.

Figure 4C:
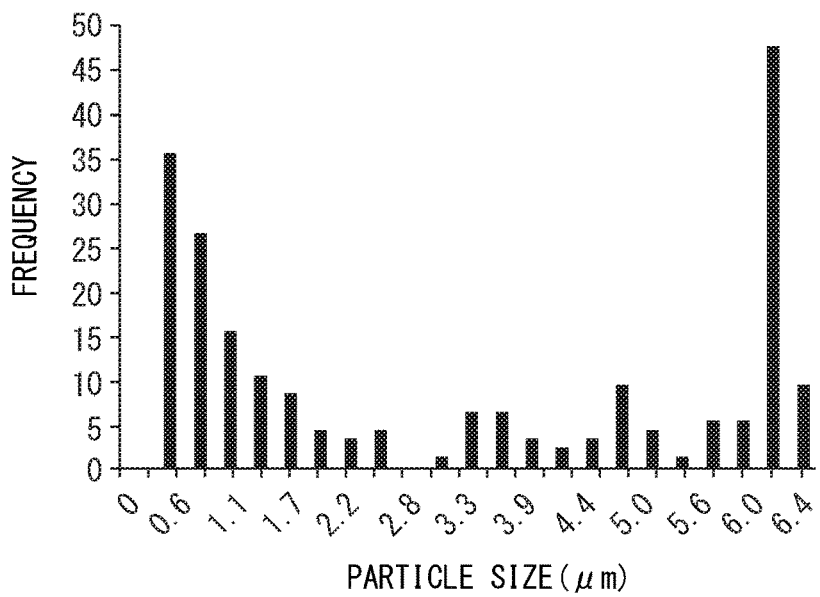
FIG. 4C is a diagram (No. 3) of measurement results of the particle size distribution.

Next, without supplying electric power to the heater H disposed in the first flow passage F1, in other words, in a state in which an ascending air stream was not formed in the first flow passage F1, measurement of the particle size distribution was performed using the particle measurement unit 10a. FIG. 4C depicts measurement results. In measurement of FIG. 4C, with respect to the first flow passage F1, an ascending air stream is not formed. It is understood that the measurement results in FIG. 4C are completely different from the measurement results in FIGS. 4A and 4B, and measurement of the particle size distribution fails to be normally performed. Thus, to measure particles, a heating unit is to be disposed.

Figure 4D:
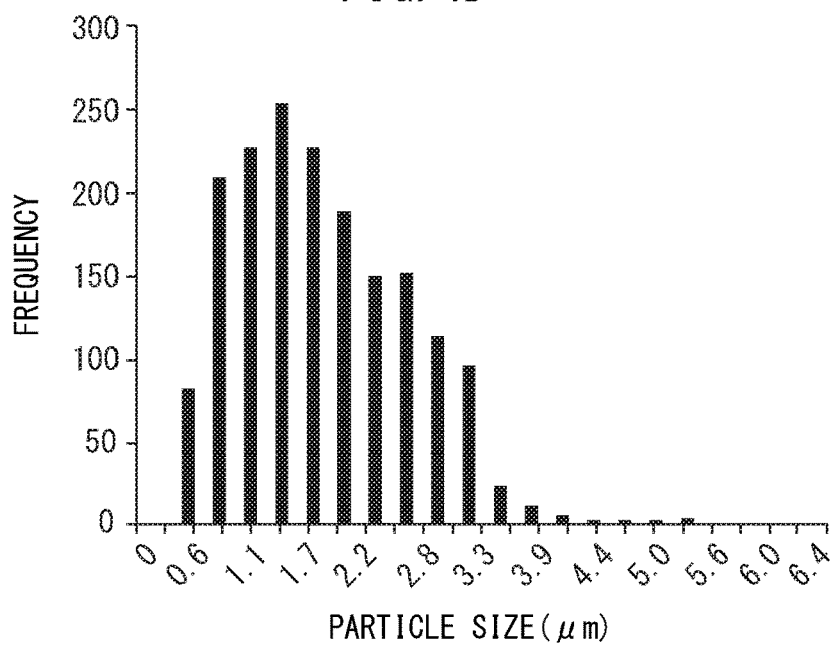
FIG. 4D is a diagram (No. 4) of measurement results of the particle size distribution.

A reason why a difference in the particle size distribution occurs between the measurement results in FIG. 4A and the measurement results in FIG. 4B can be considered that the flow rate of the first flow passage F1 is lower in a case of FIG. 4A. In measurement of particles using the Mie scattering theory, a light-receiving element outputs a pulse signal while receiving scattering light due to particles. In measurement of FIG. 4A, since the flow rate of the first flow passage F1 is smaller and a movement speed of particles is lower than measurement of FIG. 4B, a time to receive light scattered by particles having the same particle size is estimated to be longer than that in the measurement of FIG. 4B. To the measurement results in FIG. 4A, such correction so as to reduce a time of the pulse signal outputted by the light-receiving element was made. Results after the correction are depicted in FIG. 4D. In the measurement results depicted in FIG. 4D, the particle size distribution substantially in agreement with the measurement results depicted in FIG. 4B is obtained.

In the measurement device 10, an air stream is formed in the first flow passage F1 using the heating unit 17 so that a heater or a pump which has been disposed to form an air stream in conventional particle measurement devices are unnecessary. Thus, the measurement device 10 can reduce electric power for driving such heater or pump.

Next, results of measurement of a gas using the gas measurement unit 10b of the measurement device 10 as depicted in FIG. 1 will be described below.

In a state in which the temperature of the first surface 15a of the gas detection unit 15 was maintained to be a predetermined temperature using the heating unit 17, a concentration of ozone generated at a predetermined concentration by an ozone generation device separately provided was measured. As a result, it was confirmed that the gas measurement unit 10b can measure the ozone concentration in a range between 20 ppb and 200 ppb.

A gas containing ozone generated by the ozone generation device is taken in through the air inlet ports 11a of the measurement device 10 to inside the housing 11, flows to the second flow passage F2, and is detected by the first surface 15a of the gas detection unit 15 which is exposed to the second flow passage F2. An air stream for measuring such a gas is formed by heat in which the heating unit 17 heats the first surface 15a of the gas detection unit 15.

In conventional gas measurement devices, a pump for forming an air stream has been provided, whereas in the measurement device 10, such a pump is unnecessary. For example, in conventional gas measurement devices, consumed electric power of the pump for forming an air stream is approximately 200 mW. In the measurement device 10 according to the present embodiment, electric power for driving a pump can be reduced.

Further, in conventional particle measurement devices, consumed electric power of a heater disposed to form an air stream is approximately 600 mW. Thus, using the measurement device 10, electric power of approximately 800 mW in total can be reduced.

Next, a control of the heating unit 17 when particles are measured and when a gas is measured will be described below with reference to the drawings.

The flow rate of the first flow passage F1 when particles are measured is determined to be a value suitable for measurement of particles having a predetermined particle size. Similarly, the flow rate of the second flow passage F2 when a gas is measured is determined to be a value suitable for measurement of a predetermined gas.

In the measurement device 10, when the distance L2 is configured to fall within the range between ⅜ and ⅞ of the first circle reduced diameter D1 of the first flow passage F1, the flow rate of the first flow passage F1 and the flow rate of the second flow passage F2 are substantially similar values.

When the flow rate of the first flow passage F1 when particles are measured and the flow rate of the second flow passage F2 when a gas is measured are similar values, measurement of particles and measurement of a gas can be performed at the same time.

Figure 5A:
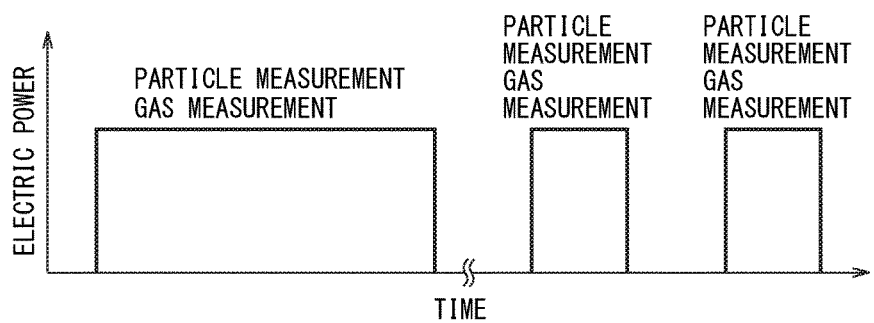
FIG. 5A is a diagram (No. 1) illustrating a control of a heating unit.

FIG. 5A is a diagram of a control of the heating unit when electric power supplied to the heating unit 17 is constant.

Since the flow rate when particles are measured and the flow rate when a gas is measured are substantially the same, as the quantity of generated heat of the heating unit 17, a constant value can be used. A time to supply electric power to the heating unit 17 can be suitably determined in accordance with a measurement time.

On the other hand, when the flow rate of the first flow passage F1 when particles are measured and the flow rate of the second flow passage F2 when a gas is measured are different from each other, the quantity of generated heat of the heating unit 17 is also different, and accordingly, measurement of particles and measurement of a gas are separately performed.

Figure 5B:
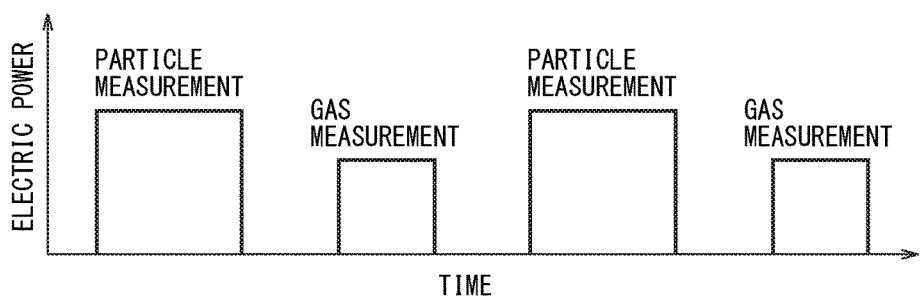
FIG. 5B is a diagram (No. 2) illustrating a control of the heating unit.

FIG. 5B is a diagram of a control of the heating unit when electric power supplied to the heating unit 17 is changed.

Since the flow rate of the second flow passage F2 when particles are measured is not a value suitable for measurement of a predetermined gas, while particles are measured, measurement of a gas is not performed. Similarly, since the flow rate of the first flow passage F1 when a gas is measured is not a value suitable for measurement of particles having a predetermined particle size, while a gas is measured, measurement of particles is not performed.

For example, as depicted in FIG. 5B, the heating unit 17 can be controlled in such a manner that measurement of particles and measurement of a gas are alternately performed.

The quantity of generated heat of the heating unit 17 is controlled such that the flow rate of the first flow passage F1 when particles are measured is a value suitable for measurement of particles having a predetermined particle size. Similarly, the quantity of generated heat of the heating unit 17 is controlled such that the flow rate of the second flow passage F2 when a gas is measured is a value suitable for measurement of a predetermined gas. Accordingly, the quantity of generated heat of the heating unit 17 is controlled such that a temperature of the second surface 15b of the gas detection unit 15 differs depending on when particles are measured and when a gas is measured. Thus, the heating unit 17 is controlled such that the temperature of the second surface 15b of the gas detection unit 15 differs depending on when particles are measured and when a gas is measured.

The above measurement device 10 which measures particles and a gas according to the present embodiment is small and consumes small electric power. Further, the measurement device 10 according to the present embodiment has a simple configuration and can be manufactured at a low manufacturing cost.

Although in the first embodiment as described above, in the first flow passage F1, a cross-sectional area is constant in the longitudinal direction, the cross-sectional area of the first flow passage F1 may not be constant from the inlet to an outlet. Also in such a case, there is preferably the relationship in which distance L2 between the first surface 15a of the gas detection unit 15 which is exposed to the second flow passage F2 and the portion of the second flow passage F2 opposite to the first surface is smaller than the first circle reduced diameter D1 when the cross-sectional shape of the first flow passage F1 is circular. For example, the cross-sectional area of the first flow passage F1 may be configured in such a manner that the cross-sectional area is larger at an outlet side than at an inlet side.

Next, another embodiment of the above measurement device will be described below with reference to FIGS. 6 to 10. The detailed description of the first embodiment given above suitably applies to those parts of another embodiment that are not specifically described herein. Further, the same component elements are designated by the same reference numerals.

Figure 6:
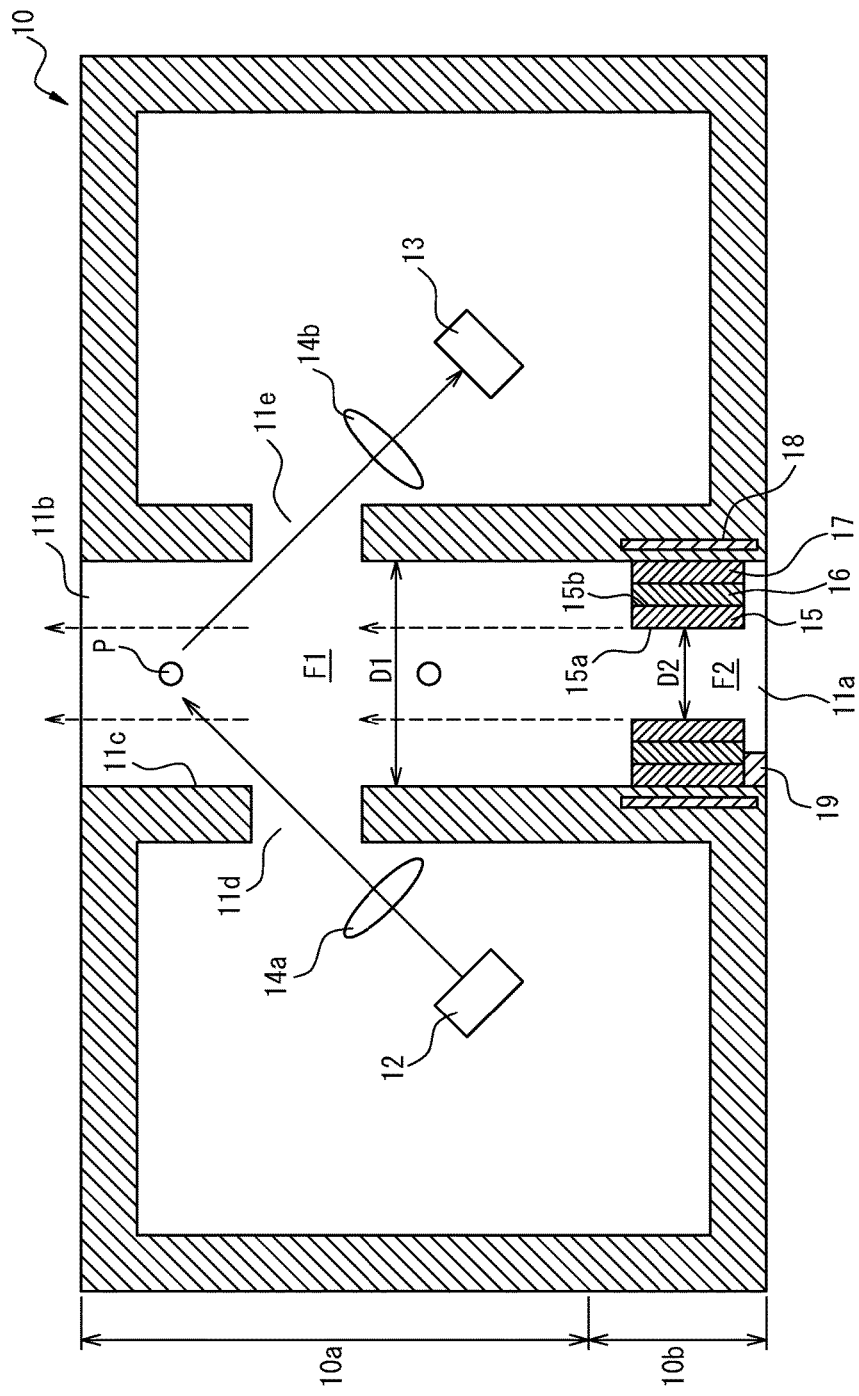
FIG. 6 is a cross-sectional view of a second embodiment of the measurement device disclosed in the present description.
Figure 7:
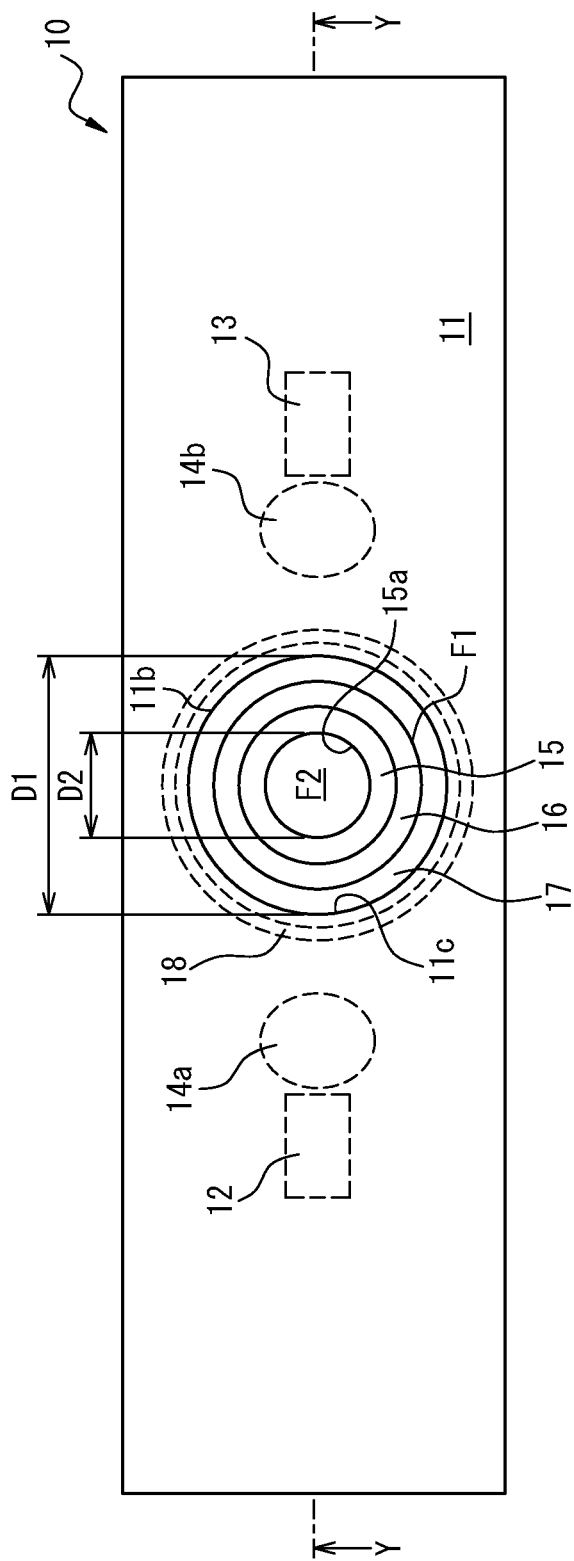
FIG. 7 is a plan view of the second embodiment of the measurement device disclosed in the present description.

FIG. 6 is a cross-sectional view of a second embodiment of the measurement device disclosed in the present description. FIG. 7 is a plan view of the second embodiment of the measurement device disclosed in the present description. FIG. 6 is the cross-sectional view taken along a line Y-Y of FIG. 7.

The measurement device 10 according to the present embodiment differs from the above first embodiment in shape of the gas measurement unit 10b and the second flow passage F2.

The gas detection unit 15, the electrical insulation part 16, and the heating unit 17 have a concentric cylindrical shape. The gas measurement unit 10b is formed by superposing the gas detection unit 15, the electrical insulation part 16, and the heating unit 17 in this order from inside. The heating unit 17 is disposed in such a manner as to fit on an extended portion of the inner wall 11c which defines the first flow passage F1.

The second flow passage F2 is disposed in such a manner as to extend the first flow passage F1 from the inlet F1a outward.

The second flow passage F2 is formed by a column-shaped space enclosed by the first surface 15a of the gas detection unit 15. The first surface 15a of the gas detection unit 15 encloses the second flow passage F2.

In the interior of the housing 11 on a side, with respect to the heating unit 17, opposite to the gas detection unit 15, the thermal insulation part 18 having a cylindrical shape is disposed.

An ascending air stream formed in the first flow passage F1 is preferably formed in such a manner as to have a flow rate capable of carrying particles having a particle size in a measurement target. From such point of view, a second circle reduced diameter D2 when a cross-sectional shape of the second flow passage F2 is circular is preferably smaller than the first circle reduced diameter D1 when the cross-sectional shape of the first flow passage F1 is circular. Herein, a cross section of the second flow passage F2 signifies a surface orthogonal to a longitudinal direction of the second flow passage F2 (direction in which the gas flows).

From a reason similar to that described on the preferable range of the distance L2 using FIG. 3, the second circle reduced diameter D2 when the cross-sectional shape of the second flow passage F2 is circular preferably falls within the range between $2/8$ and $7/8$ of the first circle reduced diameter D1 when the cross-sectional shape of the first flow passage F1 is circular. Particularly, the second circle reduced diameter D2 is preferably configured to fall within the range between $3/8$ and $5/8$, further within the range between $3/8$ and $4/8$ of the first circle reduced diameter D1.

The above measurement device 10 according to the present embodiment, effects similar to that in the above first embodiment can be obtained.

Next, a modification example 1 and a modification example 2 of the above measurement device according to the second embodiment will be described below with reference to the drawings.

Figure 8:
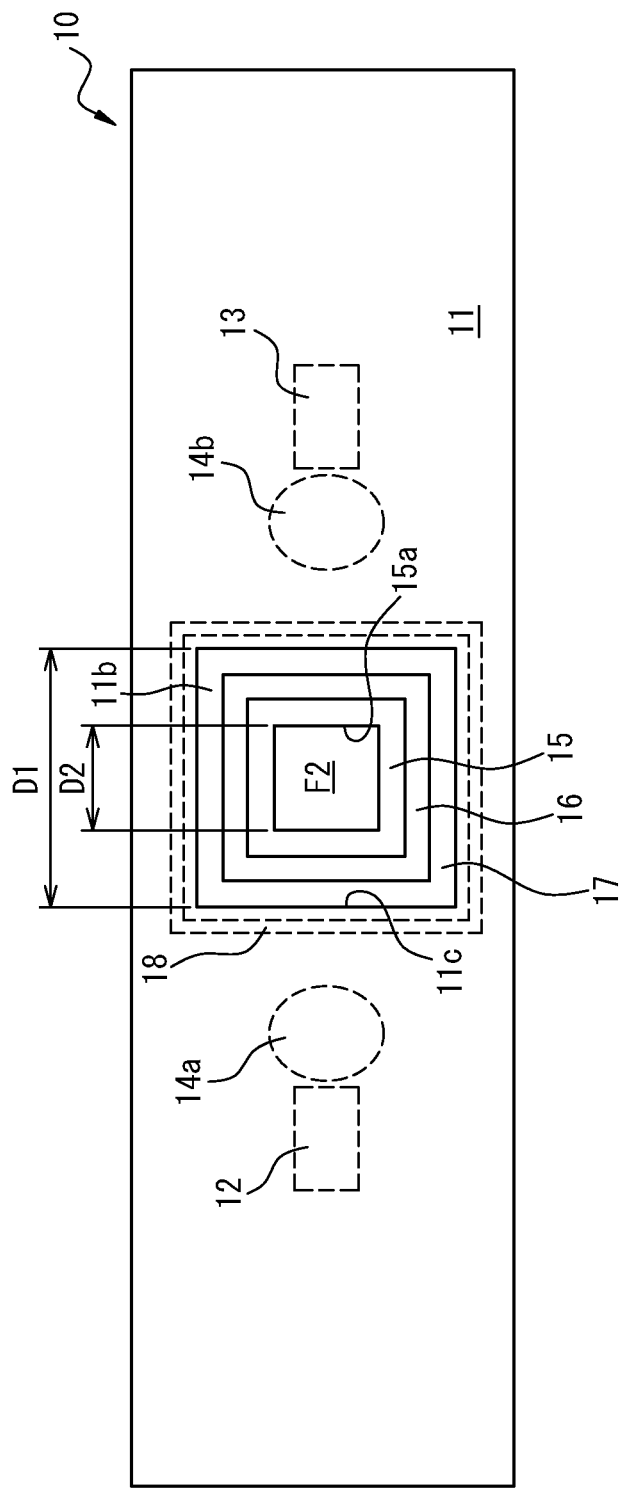
FIG. 8 is a plan view of a modification example 1 of the measurement device according to the second embodiment.

FIG. 8 is a plan view of the modification example 1 of the measurement device according to the second embodiment.

The measurement device according to the modification example 1 differs from the above second embodiment in shape of the second flow passage F2.

In the gas measurement unit 10b according to the present modification example, the gas detection unit 15, the electrical insulation part 16, and the heating unit 17 have a concentric rectangular barrel shape. The gas measurement unit 10b is formed by superposing the gas detection unit 15, the electrical insulation part 16, and the heating unit 17 in this order from inside.

The second flow passage F2 is formed by a square pole-shaped space enclosed by the first surface 15a of the gas detection unit 15. The first surface 15a of the gas detection unit 15 encloses the second flow passage F2.

The second circle reduced diameter D2 when the cross-sectional shape of the second flow passage F2 is circular is preferably smaller than the first circle reduced diameter D1 when the cross-sectional shape of the first flow passage F1 is circular.

Figure 9:
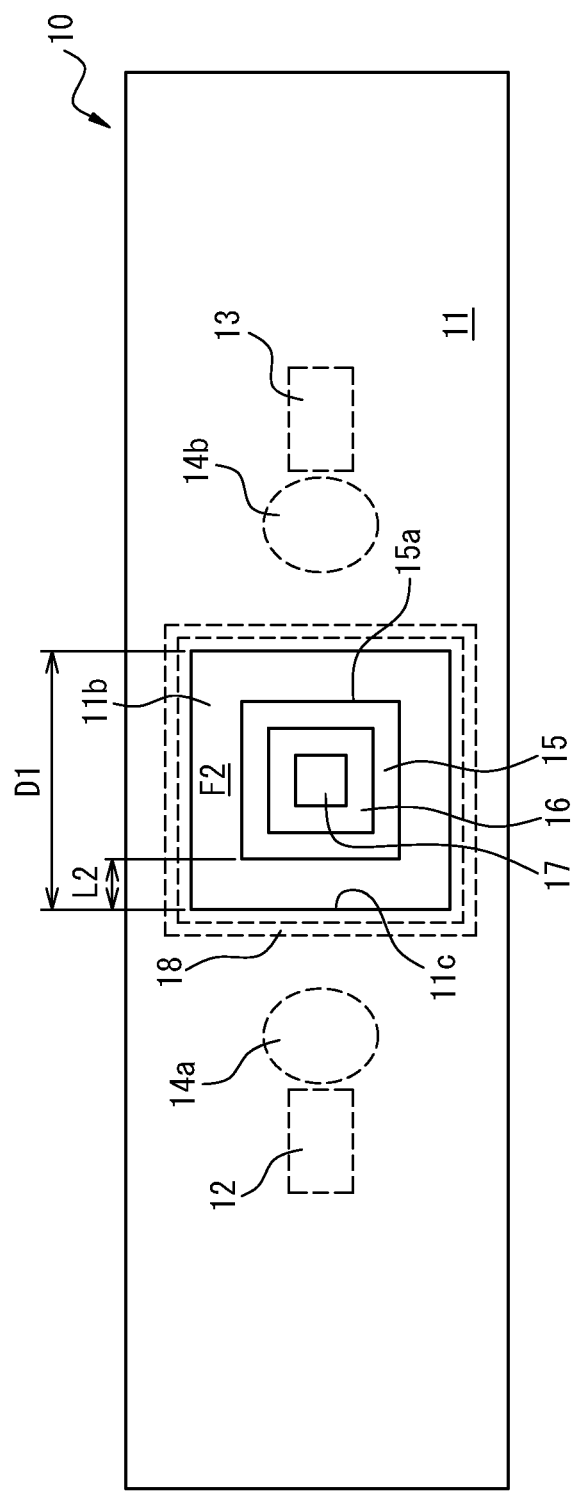
FIG. 9 is a plan view of a modification example 2 of the measurement device according to the second embodiment.

FIG. 9 is a plan view of the modification example 2 of the measurement device according to the second embodiment.

The measurement device according to the modification example 2 differs from the above second embodiment in shape of the gas measurement unit 10b and the second flow passage F2.

In the gas measurement unit 10b according to the present modification example, the electrical insulation part 16 has a rectangular barrel shape and fits around the heating unit 17. The gas detection unit 15 also has a rectangular barrel shape and fits around the electric insulation part 16. The gas measurement unit 10b is formed by superposing the heating unit 17, the electric insulation part 16, and the gas detection unit 15 in this order from inside.

The second flow passage F2 is formed by a rectangular barrel-shaped space enclosed by the inner wall 11c of the housing 11 and the first surface 15a of the gas detection unit 15. The second flow passage F2 encloses the first surface 15a of the gas detection unit 15.

The distance L2 between the first surface 15a of the gas detection unit 15 which is exposed to the second flow passage F2 and the portion of the second flow passage F2 opposite to the first surface is preferably smaller than the first circle reduced diameter D1 when the cross-sectional shape of the first flow passage F1 is circular.

Figure 10:
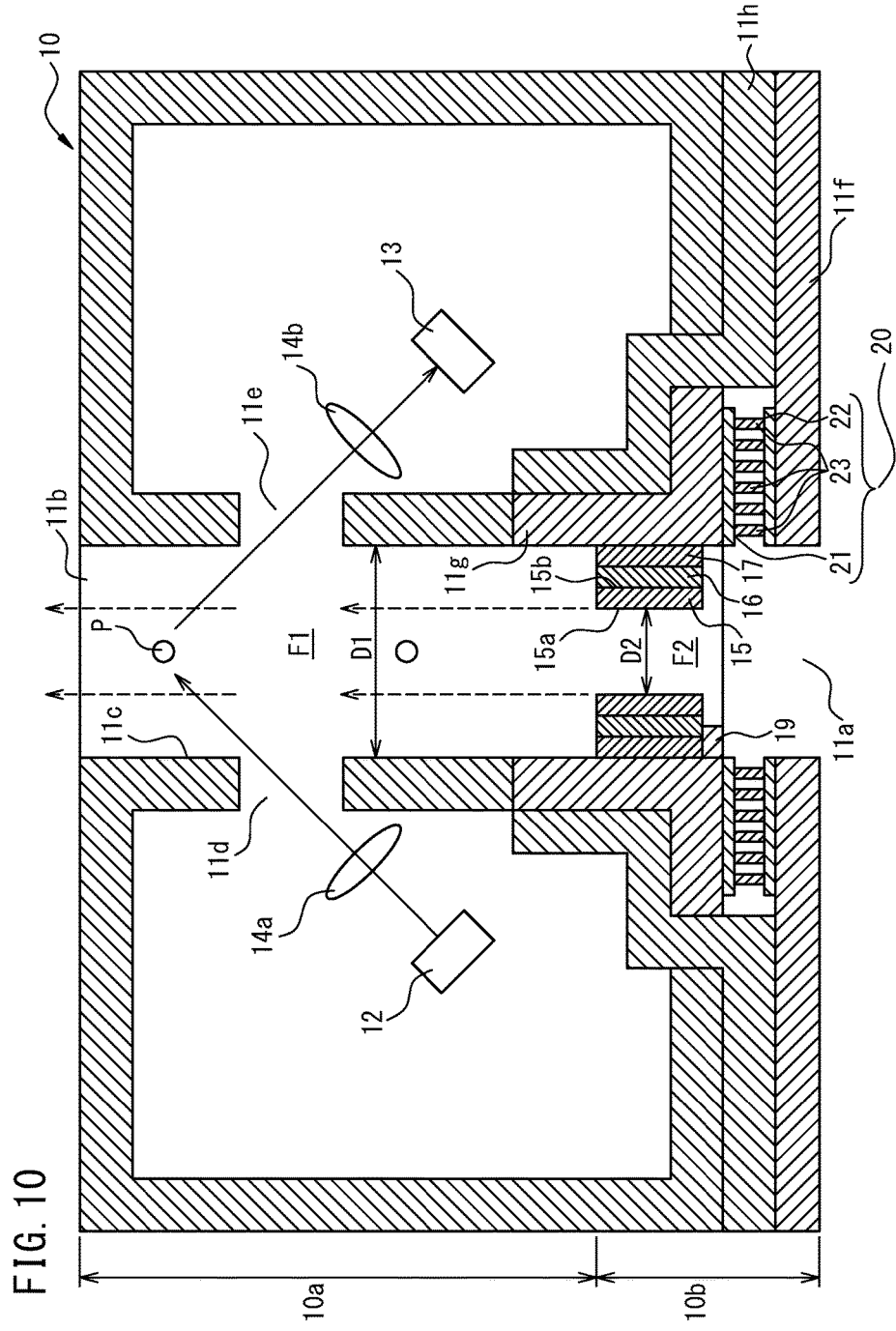
FIG. 10 is a cross-sectional view of a third embodiment of the measurement device disclosed in the present description.

FIG. 10 is a cross-sectional view of a third embodiment of the measurement device disclosed in the present description.

The measurement device 10 according to the present embodiment includes a thermoelectric conversion unit 20 to which electric power is supplied, thereby absorbing heat in the exterior and radiating heat in such a manner as to heat the second surface 15b of the gas detection unit 15.

The thermoelectric conversion unit 20 includes a first electrode layer 21, a second electrode layer 22, and a thermoelectric conversion element 23. The thermoelectric conversion element 23 is disposed between the first electrode layer 21 and the second electrode layer 22 and is supplied with the electric current, thereby transferring heat on a side of a second electrode layer 22 to a first electrode layer side. As the thermoelectric conversion element 23, for example, a Peltier element can be used.

To the first electrode layer 21 and the second electrode layer 22, the unillustrated control unit supplies electric power, whereby the thermoelectric conversion unit 20 is controlled.

At outside of the second electrode layer 22, a heat absorption part 11f is disposed. Between the first electrode layer 21 and the heating unit 17, a heat radiation part 11g is disposed. The thermoelectric conversion unit 20 absorbs heat in the exterior through the heat absorption part 11f and transfers heat as absorbed to the heating unit 17 through the heat radiation part 11g. The heating unit 17 heats the second surface 15b of the gas detection unit 15 using heat as received from the heat radiation part 11g and heat as generated by itself.

At outside the heat radiation part 11g and the heat absorption part 11f, a thermal insulation part 11h is disposed, which prevents heat from transferring from the heat radiation part 11g and the heat absorption part 11f to the others.

In the above description, the heat absorption part 11f absorbs heat in the exterior, but the heat absorption part 11f may be configured to absorb heat of the inner wall 11c, the light-emitting element 12, or the light-receiving element 13 which is heated by a heated ascending air stream.

In the above measurement device 10 according to the present embodiment, consumed electric power at the heating unit 17 can be reduced. Further, in the measurement device 10 according to the present embodiment, effects similar to that in the above first embodiment can be obtained.

Next, an embodiment of a measurement system provided with the above measurement device will be described below with reference to FIG. 11.

A measurement system 50 according to the present embodiment includes the plurality of measurement devices 10 and a server 51 communicably connected to the plurality of measurement devices 10 via a network. The measurement system 50 is a system which measures an atmospheric contamination state at multi-points.

Each measurement device 10 includes the particle measurement unit 10a, the gas measurement unit 10b, the communication unit 10c, and the control unit 10d which controls each part. As a configuration of the particle measurement unit 10a and the gas measurement unit 10b, any measurement device according to the above embodiments can be applied.

The communication unit 10c is controlled by the control unit 10d and communicates with the server 51 via the network using wired or wireless communication.

Each measurement device 10 measures the particle size distribution and the particle concentration of particulate matter in the air at a placement position, and the concentration of a gas, such as ozone, and transmits a value as measured to the server 51 via the network.

Each measurement device 10 is, for example, disposed in the vicinity of a generation source of atmospheric contaminants such as a factory, a road, or the like, and measures an atmospheric contamination state. Further, each measurement device 10 may be disposed inside a building or a site of a school or a commercial facility, and measure the environment. In addition, each measurement device 10 may be used to measure the external air outside the building and control the air condition in the building based on measurement results.

The server 51 inputs and stores measurement results of each measurement device 10, while processing measured values and outputting the same as an atmospheric contamination state. Further, the server 51 may generate an alarm based on the atmospheric contamination state. In addition, the server 51 may transmit the atmospheric contamination state to an upstream host server (unillustrated) or a data center (unillustrated).

From the point of view of improving accuracy of measuring atmospheric contaminants, a β-ray absorption type particle measurement device 52 or an ultraviolet ray absorption type gas concentration measurement device 53 having high measurement accuracy may be disposed in such a manner as to be connected to the network. Measurement results of the β-ray absorption type particle measurement device 52 or the ultraviolet ray absorption type gas concentration measurement device 53 can be inputted to the server 51 via the network and used to correct the measurement results of each measurement device 10.

The above measurement system 50 according to the present embodiment, a system which measures an atmospheric contamination state at multi-points using the plurality of measurement devices which are small and consume small electric power can be constructed in an inexpensive manner.

In the present invention, the measurement device, the measurement system, and the measurement method for measuring particles and a gas according to the above embodiments can be suitably changed without departing from the gist of the present invention. Further, it is possible to appropriately apply the component of one of the embodiments to the other embodiment.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of superiority and inferiority of the invention. Although the embodiments of the present invention have been described in detail, it should be understood that the various changes, substitutions, and alterations could be made hereto without departing from the spirit and scope of the present invention.

REFERENCE SIGNS LIST

10 Sensor
10a Particle measurement unit
10b Gas measurement unit
10c Communication unit
10d Control unit
11 Housing
11a Air inlet port
11b Air outlet port 11c Inner wall
11d Opening
11e Opening
11f Heat absorption part
11g Heat radiation part
11h Thermal insulation part
12 Light-emitting element
13 Light-receiving element
14a, 14b Lens
15 Gas detection unit
15a First surface
15b Second surface
16 Electrical insulation part
17 Heating unit
18 Thermal insulation part
19 Temperature and humidity measurement unit
20 Thermoelectric conversion unit
21 First electrode layer
22 Second electrode layer
23 Thermoelectric conversion element
50 Measurement system
51 Server
52 β-ray absorption type particle measurement device
F1 First flow passage
F1a Inlet of first flow passage
F2 Second flow passage
H Heater

What is claimed is:

1. A measurement device, comprising:
   a first flow passage;
   a heating unit provided on one end side of the first flow passage;
   a gas detection unit which is provided on the one end side of the first flow passage and capable of detecting a gas through heat applied from the heating unit;
   a particle measurement unit which optically measures, at an upper side than the heating unit of the first flow passage, particles passing through the first flow passage; and
   a second flow passage which supplies an external air to the one end of the first flow passage, wherein
   the gas detection unit includes a first surface and a second surface in which the first surface is exposed to the second flow passage, and a gas is adsorbed to the first surface, whereby an electric resistance changes, and
   the heating unit heats the second surface of the gas detection unit, and
   the first surface of the gas detection unit is disposed in such a manner as to face an inlet of the first flow passage on the one end side, and
   the second flow passage is formed by a space between the first surface of the gas detection unit and the inlet of the first flow passage on the one end side.

2. The measurement device according to claim 1, wherein a second circle reduced diameter when a cross-sectional shape of the second flow passage is circular is smaller than a first circle reduced diameter when a cross-sectional shape of the first flow passage is circular, or a distance between the first surface of the gas detection unit, the first surface being exposed to the second flow passage, and a portion of the second flow passage opposite to the first surface is smaller than the first circle reduced diameter of the first flow passage.

3. The measurement device according to claim 2, wherein the second circle reduced diameter when the cross-sectional shape of the second flow passage is circular falls within a range between $2/8$ and $7/8$ of the first circle reduced diameter when the cross-sectional shape of the first flow passage is circular, or the distance between the first surface of the gas detection unit, the first surface being exposed to the second flow passage, and the portion of the second flow passage opposite to the first surface falls within a range between $2/8$ and $7/8$ of the first circle reduced diameter of the first flow passage.

4. The measurement device according to claim 1, wherein the first surface of the gas detection unit encloses the second flow passage.

5. The measurement device according to claim 1, wherein the second flow passage encloses the first surface of the gas detection unit.

6. The measurement device according to claim 1, further comprising a thermoelectric conversion unit to which electric power is supplied, thereby absorbing heat and radiating heat in such a manner as to heat the second surface of the gas detection unit.

7. The measurement device according to claim 1, wherein on a side, with respect to the heating unit, opposite to the gas detection unit, a thermal insulation part is disposed.

8. The measurement device according to claim 1, wherein the particle measurement unit includes a light-emitting element which irradiates the first flow passage with light and a light-receiving element which receives scattering light as scattered by particles passing through the first flow passage.

9. A measurement system, comprising:
   a plurality of measurement devices, the measurement device comprising:
   a first flow passage;
   a heating unit provided on one end side of the first flow passage;
   a gas detection unit which is provided on the one end side of the first flow passage and capable of detecting a gas through heat applied from the heating unit;
   a particle measurement unit which optically measures, at an upper side than the heating unit of the first flow passage, particles passing through the first flow passage; and
   a second flow passage which supplies an external air to the one end of the first flow passage, wherein
   the gas detection unit includes a first surface and a second surface in which the first surface is exposed to the second flow passage, and a gas is adsorbed to the first surface, whereby an electric resistance changes, and
   the heating unit heats the second surface of the gas detection unit, and
   the first surface of the gas detection unit is disposed in such a manner as to face an inlet of the first flow passage on the one end side, and
   the second flow passage is formed by a space between the first surface of the gas detection unit and the inlet of the first flow passage on the one end side; and
   a server communicably connected to each measurement device.

10. A measurement method of a measurement device, the measurement device comprising:
    a first flow passage;
    a heating unit provided on one end side of the first flow passage;
    a gas detection unit which is provided on the one end side of the first flow passage and capable of detecting a gas through heat applied from the heating unit;

a particle measurement unit which optically measures, at an upper side than the heating unit of the first flow passage, particles passing through the first flow passage; and a second flow passage which supplies an external air to the one end of the first flow passage, wherein the gas detection unit includes a first surface and a second surface in which the first surface is exposed to the second flow passage, and a gas is adsorbed to the first surface, whereby an electric resistance changes, and the heating unit heats the second surface of the gas detection unit, and the first surface of the gas detection unit is disposed in such a manner as to face an inlet of the first flow passage on the one end side, and the second flow passage is formed by a space between the first surface of the gas detection unit and the inlet of the first flow passage on the one end side; and wherein the measurement method comprises controlling the heating unit such that temperatures of the gas detection unit differs depending on when particles are measured and when a gas is measured.

\* \* \* \* \*